(12) United States Patent
Gruytch

(10) Patent No.: US 9,408,799 B2
(45) Date of Patent: Aug. 9, 2016

(54) AEROSOL ANTIPERSPIRANTS

(71) Applicant: Colgate-Palmolive Company, Piscataway, NJ (US)

(72) Inventor: Robert Gruytch, Roselle Park, NJ (US)

(73) Assignee: Colgate-Palmolvie Company, New York, NY (US)

( * ) Notice: Subject to any disclaimer, the term of this patent is extended or adjusted under 35 U.S.C. 154(b) by 0 days.

(21) Appl. No.: 14/779,952

(22) PCT Filed: Apr. 19, 2013

(86) PCT No.: PCT/US2013/037284
§ 371 (c)(1),
(2) Date: Sep. 24, 2015

(87) PCT Pub. No.: WO2014/171948
PCT Pub. Date: Oct. 23, 2014

(65) Prior Publication Data
US 2016/0081910 A1    Mar. 24, 2016

(51) Int. Cl.
| | |
|---|---|
| *A61K 8/895* | (2006.01) |
| *A61K 8/04* | (2006.01) |
| *A61K 8/41* | (2006.01) |
| *A61K 8/891* | (2006.01) |
| *A61K 8/37* | (2006.01) |
| *A61K 8/26* | (2006.01) |
| *A61K 8/31* | (2006.01) |
| *A61K 8/58* | (2006.01) |
| *A61Q 15/00* | (2006.01) |

(52) U.S. Cl.
CPC .............. *A61K 8/895* (2013.01); *A61K 8/046* (2013.01); *A61K 8/26* (2013.01); *A61K 8/31* (2013.01); *A61K 8/37* (2013.01); *A61K 8/416* (2013.01); *A61K 8/585* (2013.01); *A61K 8/891* (2013.01); *A61Q 15/00* (2013.01); *A61K 2800/48* (2013.01); *A61K 2800/594* (2013.01)

(58) Field of Classification Search
CPC . A61K 2800/594; A61K 8/046; A61K 8/891; A61K 8/895; A61Q 15/00
See application file for complete search history.

(56) References Cited

U.S. PATENT DOCUMENTS

| | | | |
|---|---|---|---|
| 4,152,416 | A | 5/1979 | Spitzer et al. |
| 4,174,386 | A | 11/1979 | Spitzer et al. |
| 4,806,338 | A | 2/1989 | Smith |
| 4,935,224 | A | 6/1990 | Russo et al. |
| 5,082,652 | A | 1/1992 | Mayfield et al. |
| 5,281,409 | A | 1/1994 | Thayer et al. |
| 6,375,937 | B1 | 4/2002 | Chopra et al. |
| 6,582,683 | B2 | 6/2003 | Jezior |
| 6,960,338 | B2 | 11/2005 | Li et al. |
| 7,074,394 | B2 | 7/2006 | Li et al. |
| 7,105,691 | B2 | 9/2006 | Holerca et al. |
| 7,407,666 | B2 | 8/2008 | Tarletsky et al. |
| 2004/0109833 | A1 | 6/2004 | Tang et al. |
| 2004/0198998 | A1 | 10/2004 | Holerca et al. |
| 2006/0204463 | A1 | 9/2006 | Tang et al. |
| 2006/0210486 | A1* | 9/2006 | Esposito ................ A61K 8/042 424/47 |
| 2007/0243143 | A1 | 10/2007 | Patil et al. |
| 2008/0187504 | A1 | 8/2008 | Fan et al. |
| 2011/0250249 | A1 | 10/2011 | Mateu et al. |
| 2012/0003165 | A1 | 1/2012 | Mateu et al. |
| 2012/0014882 | A1* | 1/2012 | Singleton ................ A61K 8/34 424/45 |

FOREIGN PATENT DOCUMENTS

| | | |
|---|---|---|
| WO | WO 98/13014 | 4/1998 |
| WO | WO 2004/078125 | 9/2004 |
| WO | WO 2007/100689 | 9/2007 |
| WO | WO 2011/034630 | 3/2011 |
| WO | WO 2012/009405 | 1/2012 |

OTHER PUBLICATIONS

O'Lenick Jr. Comparatively Speaking: Dimethicone/Vinyl Dimethicone Copolymer vs. Bis-Vinyldimethicone/Dimethicone Copolymer. Cosmetics and Toiletries Science Applied; Sep. 1, 2009.*
International Search Report & Written Opinion for International Application No. PCT/US2013/037284 issued on Feb. 3, 2014.

* cited by examiner

*Primary Examiner* — Anna Falkowitz

(57) ABSTRACT

An aerosol antiperspirant composition comprising: at least one active antiperspirant ingredient, a bis-vinyl dimethicone/dimethicone copolymer, a silicone solvent, at least one fatty acid ester and at least one propellant.

25 Claims, No Drawings

AEROSOL ANTIPERSPIRANTS

BACKGROUND

Antiperspirant compositions are generally applied to an axillary region of a subject person to limit perspiration and/or to limit or kill bacteria in this region. In this way, body odour caused by bacterial growth is eliminated or at least reduced.

Antiperspirants can be delivered topically in liquid form as an aerosol. When these compositions are applied to the axillary region, the aerosol spray is deposited as fine droplets on the skin. Some of the droplets may be dispersed laterally in the spray and/or bounce off the skin, and so may not be deposited to form an effective antiperspirant layer on the skin. Such a dispersed spray/bounce-back phenomenon reduces the antiperspirant, anti-wetness efficacy of the aerosol antiperspirant composition by delivering less antiperspirant to the skin.

There is therefore a need to provide improved aerosol antiperspirant compositions which have enhanced deposition on the skin and which can enhance the antiperspirant, anti-wetness efficacy of the aerosol antiperspirant composition.

BRIEF SUMMARY

In a first aspect, provided is an aerosol antiperspirant composition comprising: at least one active antiperspirant ingredient, a bis-vinyl dimethicone/dimethicone copolymer, a silicone solvent, at least one fatty acid ester and at least one propellant.

It has been found by the present inventors that the use, in an aerosol antiperspirant composition comprising at least one active antiperspirant ingredient and at least one propellant, of the combination of a bis-vinyl dimethicone/dimethicone copolymer, a silicone solvent, and at least one fatty acid ester, can increase the deposition of the at least one active antiperspirant ingredient on an axillary area of a subject from a dose of an aerosol spray comprising the composition.

Optionally, the bis-vinyl dimethicone/dimethicone copolymer is present in an amount of from 0.1 to 0.75 wt %, further optionally from 0.15 to 0.3 wt %, typically from 0.2 to 0.25 wt %, based on the weight of the composition including the at least one propellant.

Optionally, the silicone solvent comprises dimethicone.

Optionally, the silicone solvent is present in an amount of from 0.5 to 5 wt %, further optionally from 0.75 to 2 wt %, typically from 0.9 to 1.25 wt %, based on the weight of the composition including the at least one propellant.

Optionally, the at least one fatty acid ester comprises one or more esters of a C2-C5 alcohol and a C12-C20 fatty acid. In some embodiments, the C2-C5 alcohol comprises propyl alcohol. In some embodiments, the C12-C20 fatty acid comprises at least one fatty acid selected from myristic acid, palmitic acid and isostearic acid. In some embodiments, the at least one fatty acid ester comprises one of more of isopropyl myristate, isopropyl palmitate and isopropyl isostearate. Typically, the at least one fatty acid ester comprises a mixture of isopropyl myristate and isopropyl palmitate.

In some embodiments, the isopropyl myristate and isopropyl palmitate are present in the mixture in a weight ratio of from 0.5:1 to 1:0.5, typically about 1:1.

Optionally, the at least one fatty acid ester is present in an amount of from 0.5 to 7.5 wt %, further optionally from 2 to 5 wt %, typically from 3 to 4.5 wt %, based on the weight of the composition including the at least one propellant.

In some embodiments, the composition further comprises a thickener comprised of an organic derivative of a hectorite clay. Optionally, the thickener comprises a trialkylaryl ammonium hectorite clay. Typically, the thickener comprises quaternium-18 hectorite. Optionally, the organic derivative of a hectorite clay is present in an amount of from 0.2 to 0.4 wt %, further optionally from 0.25 to 0.35 wt %, based on the weight of the composition including the at least one propellant.

In some embodiments, the at least one active antiperspirant ingredient is selected from aluminium salts, zirconium salts and zinc salts. Typically, the at least one active antiperspirant ingredient comprises aluminium chlorohydrate.

Optionally, the composition further comprises one or more ingredients selected from: a deodorant, a fragrance, a preservative, an emulsifier, an antioxidant and an emollient.

In a further aspect, provided is an antiperspirant composition aerosol dispenser comprising the composition packaged in an aerosol container. Typically, the container is a pressurized aerosol container.

In a further aspect, provided is the use of the composition as an antiperspirant.

In a further aspect, provided is a method comprising applying the composition to the axillary area of a subject.

In a further aspect, provided is a method of manufacturing the composition, the method including the step of: a. providing the bis-vinyl dimethicone/dimethicone copolymer, the silicone solvent, and the at least one fatty acid ester as at least one premixed gel; and b. mixing the at least one premixed gel with at least the active antiperspirant ingredient.

In a further aspect, provided is the use, in an aerosol antiperspirant composition comprising at least one active antiperspirant ingredient and at least one propellant, of the combination of a bis-vinyl dimethicone/dimethicone copolymer, a silicone solvent, and at least one fatty acid ester for increasing the deposition of the at least one active antiperspirant ingredient on an axillary area of a subject from a dose of an aerosol spray comprising the composition.

Typically, the bis-vinyl dimethicone/dimethicone copolymer, the silicone solvent, and the at least one fatty acid ester are provided as at least one premixed gel.

Optionally the composition further comprises a thickener comprised of quaternium-18 hectorite.

DETAILED DESCRIPTION

It should be understood that the detailed description and specific examples, whilst indicating embodiments of the invention, are intended for the purpose of illustration only and are not intended to limit the scope of the invention.

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. The amounts given are based on the active weight of the material Provided is an aerosol antiperspirant composition comprising: at least one active antiperspirant ingredient, a bis-vinyl dimethicone/dimethicone copolymer, a silicone solvent, at least one fatty acid ester and at least one propellant.

The bis-vinyl dimethicone/dimethicone copolymer, silicone solvent, and at least one fatty acid ester are present in an emollient-containing base for the antiperspirant composition.

The aerosol antiperspirant composition is preferably substantially anhydrous, and comprises less than 2 wt % water, typically no more than about 1 wt % water, and most typically no added water apart from any water bound to the active antiperspirant ingredient.

Emollient-Containing Base

The composition comprises an emollient-containing base. The base comprises emollients, including the at least one fatty acid ester, which may also function as gelling agents. Furthermore, the base comprises a silicone system including a bis-vinyl dimethicone/dimethicone copolymer and a silicone solvent. The base may also comprise other carrier components for the antiperspirant composition.

As described above, the silicone system includes a bis-vinyl dimethicone/dimethicone copolymer (CAS No. 156065-02-0).

In some embodiments, the bis-vinyl dimethicone/dimethicone copolymer is present in an amount of from 0.1 to 0.75 wt %, for example 0.15 to 0.3 wt %, typically from 0.2 to 0.25 wt %, based on the weight of the composition including the at least one propellant.

As described above, the silicone system includes a silicone solvent. In some embodiments, the silicone solvent comprises dimethicone. The silicone solvent may be present in an amount of from 0.5 to 5 wt %, for example from 0.75 to 2 wt %, typically from 0.9 to 1.25 wt %, based on the weight of the composition including the at least one propellant. Other silicone solvents known to those skilled in the art may be employed in addition to, or instead of, dimethicone.

As described above, the base comprises emollients, including the at least one fatty acid ester, which may also function as gelling agents.

In some embodiments, the at least one fatty acid ester comprises one or more esters of a C2-C5 alcohol and a C12-C20 fatty acid. The C2-C5 alcohol may comprise propyl alcohol and/or the C12-C20 fatty acid may comprise at least one fatty acid selected from myristic acid, palmitic acid and isostearic acid. In some embodiments, the at least one fatty acid ester comprises one of more of isopropyl myristate, isopropyl palmitate and isopropyl isostearate.

Typically, the at least one fatty acid ester comprises a mixture of isopropyl myristate and isopropyl palmitate. The isopropyl myristate and isopropyl palmitate may be present in the mixture in a weight ratio of from 0.5:1 to 1:0.5, typically about 1:1.

In some embodiments, the at least one fatty acid ester is present in an amount of from 0.5 to 7.5 wt %, further optionally from 2 to 5 wt %, typically from 3 to 4.5 wt %, based on the weight of the composition including the at least one propellant.

Typically, the bis-vinyl dimethicone/dimethicone copolymer, the silicone solvent, and the at least one fatty acid ester are provided as at least one premixed gel. The pre-mixed gel may comprise a mixture of two or more gel components, each comprising bis-vinyl dimethicone/dimethicone copolymer, silicone solvent and fatty acid ester.

A first typical gel component comprises a premixed gel including bis-vinyl dimethicone/dimethicone copolymer, dimethicone and isopropyl myristate is available in commerce for example from Jeen International Corporation, NJ. USA under the trade name Jeelux DMIPM. A suitable premix gel includes 4-11 wt %, 37-47 wt % dimethicone, and 45-55 wt % isopropyl myristate.

A second typical gel component comprises a premixed gel including bis-vinyl dimethicone/dimethicone copolymer, dimethicone and isopropyl palmitate is available in commerce for example from Jeen International Corporation, NJ. USA under the trade name Jeelux DMIPP. A suitable gel includes 5-13 wt % bis-vinyl dimethicone/dimethicone copolymer, 46-56 wt % dimethicone, and 35-45 wt % isopropyl palmitate.

In a preferred composition a mixture of these first and second gel components is employed to provide the desired amounts of the bis-vinyl dimethicone/dimethicone copolymer, the silicone solvent, and the at least one fatty acid ester. For example, a 1:1 weight ratio of these first and second gel components may be employed.

In some embodiments, the emollient-containing base further comprises other gelling agents and/or emollients. Examples of other gelling agents/emollients include, but are not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, propylene carbonate, or other cosmetically acceptable materials, which are solid or semi-solid at room temperature and provide a consistency suitable for application to the skin.

In one embodiment, the composition comprises hydrogenated soybean oil in a typical amount of up to 5 wt %, more typically from 0.2 to 2 wt %, for example from 0.5 to 0.75 wt %, based on the weight of the composition. In one embodiment, the composition comprises C12-C15 alkyl benzoate in a typical amount of up to 5 wt %, more typically from 0.5 to 2 wt %, based on the weight of the composition.

In some embodiments, the emollient-containing base further comprises a thickener comprised of an organic derivative of a hectorite clay, for example a trialkylaryl ammonium hectorite clay or quaternium-18 hectorite. In some embodiments, the organic derivative of a hectorite clay is present in an amount of from 0.2 to 0.4 wt %, typically from 0.25 to 0.35 wt %, based on the weight of the composition including the at least one propellant.

The antiperspirant composition comprises at least one active antiperspirant ingredient, and optionally at least one active deodorant ingredient.

Active Antiperspirant Ingredients

In some embodiments, the at least one active antiperspirant ingredient is selected from aluminium salts, zirconium salts and zinc salts. Any of the known aluminum containing antiperspirant active materials can be utilized in the composition of the invention.

Antiperspirant actives include, but are not limited to, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum, sesquichlorohydrate polyethylene glycol, aluminum sesquichlorohydrate propylene glycol, aluminum-zirconium octachlorohydrate, aluminum-zirconium octachlorohydrex gly, aluminum-zirconium pentachlorohydrate, aluminum-zirconium pentachlorohydrex gly, aluminum-zirconium tetrachlorohydrate, aluminum-zirconium tetrachlorohydrex gly, aluminum-zirconium trichlorohydrate, aluminum-zirconium trichlorohydrex gly, and combinations thereof. Generally, any of the Category I active antiperspirant ingredients, listed in the Food and Drug Administration's Monograph on Antiperspirant Drug Products for over-the-counter human use (Oct. 10, 1973) can be used (21 CFR 350.10). In one embodiment, the antiperspirant active is aluminum chlorohydrate. In another embodiment, the antiperspirant active is aluminum zirconium tetrachlorhydrex propylene glycol.

In other embodiments, the antiperspirant active is an aluminum salt and/or an aluminum-zirconium salt, such as those described above, that are further stabilized by betaine and a calcium salt. More information betaine and calcium salt stabilized antiperspirant salts can be found in U.S. Patent Application Publication No. 2006/0204463 to Tang et al. In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al. In other embodiments, the type of salt of interest, an aluminum zirconium tetrasalt or octasalt free of glycine are used wherein aluminum zirconium salt is stabilized by betaine and has a metal to chloride ratio of 0.9:1 to 1.3:1 (and in other embodiments of 0.9:1 to 1.2:1 or 0.9:1 to 1.1:1). For the tetrasalt, the Al/Zr atomic ratio can be 3.2:1 to 4.1:1.0 and the betaine:zirconium mole ratio can be 0.2:1 to 3.0:1 (or in other embodiments of 0.4:1 to 1.5:1). Another salt that can be used is an aluminum chloride salt buffered by betaine, wherein the salt has a metal to chloride ratio of 0.9:1 to 1.3:1 (and in other embodiments of 0.9:1 to 1.2:1 or 0.9:1 to 1.1:1). For the octasalt the Al Zr atomic ratio is 6.2:1 to 10.0:1 and the betaine:Zr mole ratio is 0.2:1 to 3.0:1 (or in other embodiments of 0.4:1 to 1.5:1). In one embodiment, in the case of a salt that contains zirconium, the betaine is incorporated during the synthesis of the salt so as to maximize the stabilizing effect this ingredient has (especially on the zirconium species). Alternatively, it can be post added to a glycine-free salt along with additional active phase ingredients to form a betaine stabilized active. Additionally, the antiperspirant active can be a calcium salt stabilized antiperspirant active. Examples of calcium salt stabilized antiperspirant actives can be found in U.S. Patent Application Publication No. 2006/0204463.

Examples of commercially available glycine-free low M:Cl ratio tetrasalts and octasalts include, but are not limited to, REZAL™ AZP 955 CPG and REZAL™ AZP 885 respectively (both from SummitReheis Antiperspirant Actives of Huguenot, N.Y.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

Antiperspirant actives can be incorporated into compositions in amounts of 0.5 to 25 w % (on an actives basis) of the final composition, but the amount used will depend on the formulation of the composition. Generally at lower levels the antiperspirant active material will not substantially reduce the flow of perspiration as effectively, but will reduce malodor, for example, by acting also as an antimicrobial material. In certain embodiments, the base antiperspirant material can be designed to more effectively deliver the antiperspirant to the skin. In these situations, the amount of antiperspirant can be lowered but still deliver the same level of efficacy as a product with higher levels of antiperspirant. For an example of a composition that provides the same clinical efficacy at a 10 wt % antiperspirant level as other compositions that have a 17 wt % antiperspirant level, see the hydrocarbon/hydrogenated soybean oil gelled formulation in U.S. Patent Application Publication No. 2008/0187504A1.

In certain embodiments, the amount of antiperspirant active is less than 12 wt % based on the total weight of the composition including the propellant. In other embodiments, the amount of antiperspirant active is from 0.5 to 10, 2 to 10 wt %, from 3 to 7.5 wt %, or from 4 to 5 wt %, based on the total weight of the composition including the propellant.

In certain embodiments, the composition may include any known deodorant active. Examples of deodorant actives include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammomium bromide, cetyl pyridinium chloride, farnesol (3,7,11-trimethyl-2,6,10-dodecatrien-1-ol), N-(4-chlorophenyl)-N'-(3,4-dichlorophenyl)urea (Triclocarban), silver halides, octoxyglycerin (Sensiva™ SC 50) and various zinc salts (for example, zinc ricinoleate), bactericides, and/or bacteriostats.

The deodorant active can, illustratively, be included in the composition in an amount of 0-5% wt %, or 0.01-1 wt %, based on the total weight of the composition including the propellant. Triclosan can, illustratively, be included in an amount of 0.05 to 0.5 wt %, based on the total weight of the composition including the propellant.

Other Components

Additional components of the antiperspirant compositions optionally include any components suitable for use in such compositions which are known in the art. Optionally, the composition further comprises one or more ingredients selected from: a fragrance, a preservative, an emulsifier, an antioxidant and an emollient.

Aerosol Disperser and Propellant

The aerosol antiperspirant composition is packaged in a dispenser comprising an aerosol container capable of dispensing the composition topically on to the axillary area of a subject. Such containers are known in the art. Typically, the container is a pressurized aerosol container.

The composition further comprises at least one propellant which is a liquefied gas, typically a liquefied hydrocarbon such as one or more of butane, propane and isobutane, for example a mixture of these three propellant components.

The least one propellant is typically present in an amount of from 80 to 95 wt %, for example about 85 wt %, based on the total weight of the composition.

Methods of Manufacture

The antiperspirant compositions may be manufactured using methods known in the art. Typically, the ingredients are combined and optionally heated where components need to be melted. The components are mixed. Desirably, volatile materials such as fragrant materials are incorporated in the composition in the latter stages of a mixing cycle in order to avoid volatilisation thereof. After mixing, the composition may be poured directly into the dispensers and, after propellant addition, the container is capped to preserve the product until use.

In a preferred embodiment, the bis-vinyl dimethicone/ dimethicone copolymer, the silicone solvent, and the at least one fatty acid ester are initially provided as at least one premixed gel, and thereafter the at least one premixed gel is mixed with the at least the active antiperspirant ingredient, optionally together with other additional components of the antiperspirant composition. Then the liquefied gas propellant is added and the composition packaged in an aerosol dispenser.

Specific Embodiments

This invention can be further illustrated by the following Examples of preferred embodiments thereof, although it will be understood that these Examples are included merely for purposes of illustration and are not intended to limit the scope of the invention unless otherwise specifically indicated.

Example 1

In Example 1 the aerosol antiperspirant composition of Table 1 was produced.

The two pre-mixed gel components DMIPM containing approximately 50% isopropyl myristate, 42% dimethicone, and 8% bis-vinyl dimethicone/dimethicone copolymer, and DMIPP containing approximately 51% dimethicone, 40% isopropyl palmitate, and 9% bis-vinyl dimethicone/dimethicone copolymer together provided in the composition a total amount of 1.176 wt % dimethicone and 0.224 wt % bis-vinyl dimethicone/dimethicone copolymer. The total amount of isopropyl palmitate in the composition was 2.10 wt % and the total amount of isopropyl myristate in the composition was 2.10 wt %.

TABLE 1

| Ingredient | Wt % |
| --- | --- |
| Hydrocarbon propellant mixture (Butane, propane, isobutane) | 85 |
| Activated aluminium chlorohydrate | 5.6 |
| C12-15 Alkyl benzoate | 1.82 |
| Isopropyl Palmitate | 1.4 |
| Isopropyl Myristate | 1.4 |
| DMIPP (Dimethicone, Isopropyl Palmitate, Bis-Vinyl Dimethicone/Dimethicone Copolymer) | 1.4 |
| DMIPM (Dimethicone, Isopropyl Myristate, Bis-Vinyl Dimethicone/Dimethicone Copolymer) | 1.4 |
| Fragrance | 1 |
| Hydrogenated Soybean oil | 0.57 |
| Bentone 27 (Trialkylaryl ammonium hectorite) | 0.31 |
| Propylene carbonate | 0.1 |
| Total | 100.00 |

The aerosol antiperspirant composition of Example 1 was tested to determine its deposition efficacy onto a surface representing an axillary area of a subject.

The testing was carried out by providing the aerosol antiperspirant composition in a conventional aerosol spray container, and spraying the composition onto a surface for a period of 2 seconds. The weight loss of the container was measured and the amount of the antiperspirant composition (minus the evaporated propellant) deposited onto the surface was also measured. The two measurements were compared, after accounting for the weight of propellant, to determine the proportion of the antiperspirant composition (minus the evaporated propellant) which was deposited onto the surface. This expressed a parameter, deposition efficacy, as a percentage amount of the total spray which was actually deposited on the surface. Three separate tests were carried out and the results were averaged.

For the aerosol antiperspirant composition of Example 1, it was found that there was a deposition efficacy of 85% onto the surface, as shown in Table 2.

TABLE 2

| | DMIPP/DMIPM amounts - wt % | Bis-vinyl dimethicone/dimethicone copolymer - wt % | Deposition efficacy - % deposited |
| --- | --- | --- | --- |
| Example 1 | 10/10 | 0.224 | 85 |
| Example 2 | 5/5 | 0.112 | 70 |
| Example 3 | 7.5/7.5 | 0.168 | 61 |
| Example 4 | 12.5/12.5 | 0.280 | 74 |
| Example 5 | 15/15 | 0.336 | 77 |
| Example 6 | 20/20 | 0.448 | 89 |
| Comparative Example 1 | 0/0 | 0 | 52 |
| Comparative Example 2 | 0/0 | 0 | 51 |

Examples 2 to 6

In Examples 2 to 6 the aerosol antiperspirant composition of Example 1 was modified by varying the total amounts of the two components DMIPM and DMIPP, which in turn provided varying amounts of the bis-vinyl dimethicone/dimethicone copolymer. The deposition efficacy was also measured for each of Examples 2 to 6 and the results, together with the respective amount of the bis-vinyl dimethicone/dimethicone copolymer, are shown in Table 2.

From Table 2 it may be seen that the addition of the bis-vinyl dimethicone/dimethicone copolymer tended to increase the deposition efficacy.

Comparative Examples 1 and 2

In Comparative Examples 1 and 2 aerosol antiperspirant compositions similar to Example 1 were formulated, except that these did not comprise either of the two components DMIPM and DMIPP. Accordingly, the compositions of Comparative Examples 1 and 2 comprised no bis-vinyl dimethicone/dimethicone copolymer or dimethicone.

Comparative Example 1 was formulated in the test laboratory and Comparative Examples 2 was a commercially available aerosol antiperspirant composition with soy base.

The deposition efficacy was also measured for each of Comparative Examples 1 and 2 and the results are as shown in Table 2.

From Table 2 it may be seen that in Examples 1 to 6 the addition of the bis-vinyl dimethicone/dimethicone copolymer tended to increase the deposition efficacy as compared to the compositions of Comparative Examples 1 and 2.

Without being bound by any theory, it is believed that the bis-vinyl dimethicone/dimethicone copolymer improves the deposition of the antiperspirant composition by providing cohesive forces in the mixture which result in a more compact spray, with fewer small spray droplet particles flying off laterally which would tend not to be deposited, and so in turn the compact spray is more directed towards the skin, thereby enhancing deposition efficacy. In addition, it is believed that the bis-vinyl dimethicone/dimethicone copolymer may reduce the bounce back of spray droplet particles from the skin, again thereby enhancing deposition efficacy.

Furthermore, the composition of Example 1 provided the highest deposition efficacy of all of Examples 1 to 5 when the bis-vinyl dimethicone/dimethicone copolymer amount was below about 0.4 wt % It is noticed that when the silicone copolymer is increased too high, the product leaves a tacky feeling on skin when dispensed.

Examples 7 and 8

In Examples 7 and 8 the aerosol antiperspirant composition of Example 1 was modified by alternately employing only one of the components DMIPM and DMIPP as shown in Table 3. The deposition efficacy was also measured for each of Examples 7 and 8 and the results, together with the respective amount of the bis-vinyl dimethicone/dimethicone copolymer, are shown in Table 3.

TABLE 3

|  | DMIPP/DMIPM amounts - wt % | Bis-vinyl dimethicone/ dimethicone copolymer - wt % | Deposition efficacy - % deposited |
|---|---|---|---|
| Example 7 | 0/10 | 0.112 | 72 |
| Example 8 | 10/0 | 0.112 | 67 |

From Table 3 it may be seen that the addition of the bis-vinyl dimethicone/dimethicone copolymer in either DMIPP or DMIPM had a similar deposition efficacy as compared to Example 2 which had the same total amount, 0.112 wt %, of bis-vinyl dimethicone/dimethicone copolymer and comprised a 1:1 by weight blend of DMIPP and DMIPM Examples 7 and 8 exhibited enhanced deposition efficacy as compared to Comparative Examples 1 and 2 due to the presence of the bis-vinyl dimethicone/dimethicone copolymer.

Comparative Examples 3 to 5

In Comparative Examples 3 to 5 aerosol antiperspirant compositions similar to Example 1 were formulated, except that these did not comprise either of the two components DMIPM and DMIPP. Accordingly, the compositions of Comparative Examples 5 to 7 comprised no bis-vinyl dimethicone/dimethicone copolymer but did comprise dimethicone.

Table 4 shows the amount of dimethicone in the aerosol antiperspirant compositions of Comparative Examples 3 to 5. For comparison, in Example 1 the dimethicone amount was 1.18 wt % based on the total weight of the composition including the propellant.

The deposition efficacy was also measured for each of Comparative Examples 3 to 5 and the results are shown in Table 4.

TABLE 4

|  | Dimethicone amount - wt % | Bis-vinyl dimethicone/ dimethicone copolymer - wt % | Deposition efficacy - % deposited |
|---|---|---|---|
| Comparative Example 3 | 1.20 | 0 | 69 |
| Comparative Example 4 | 1.95 | 0 | 73 |
| Comparative Example 5 | 3.00 | 0 | 80 |

From Table 4 it may be seen from a comparison of Comparative Example 3 and Example 1, which had the same amount of dimethicone, that the addition of the bis-vinyl dimethicone/dimethicone copolymer tended to increase the deposition efficacy.

Furthermore, it may be seen from a comparison of Comparative Examples 4 and 5 and Example 1 that increasing the amount of dimethicone, but in the absence of the bis-vinyl dimethicone/dimethicone copolymer, tended to increase the deposition efficacy but nevertheless the deposition efficacy was still lower than in Example 1. In other words, in Example 1 the total amount of silicone compounds, comprising dimethicone and bis-vinyl dimethicone/dimethicone copolymer, was lower than the total amount of silicone compound, comprising dimethicone, in Comparative Examples 4 and 5 but still provided enhanced deposition efficacy as a result of the addition of the bis-vinyl dimethicone/dimethicone copolymer.

Therefore a comparison of Comparative Examples 3 to 5 and Example 1 shows that the bis-vinyl dimethicone/dimethicone copolymer tended to increase the deposition efficacy to a greater degree than dimethicone.

Examples 9 to 11

In Examples 9 to 11 the aerosol antiperspirant compositions of, respectively, Examples 1, 7 and 8 were modified by substituting the Bentone 27 particulate clay thickener by Bentone 38, which is an organic derivate of hectorite clay. The respective same amounts of the components DMIPM and DMIPP were employed as shown in Table 5.

The deposition efficacy was also measured for each of Examples 9 to 11 and the results, together with the respective amount of the bis-vinyl dimethicone/dimethicone copolymer, are shown in Table 5.

TABLE 5

|  | DMIPP/DMIPM amounts - wt % | Bis-vinyl dimethicone/ dimethicone copolymer - wt % | Deposition efficacy - % deposited |
|---|---|---|---|
| Example 9 | 10/10 | 0.224 | 72 |
| Example 10 | 0/10 | 0.112 | 55 |
| Example 11 | 10/0 | 0.112 | 57 |

From Table 5 it may be seen that the Bentone 27 particulate clay thickener as used in Examples 1 to 8 tended to increase the deposition efficacy as compared the Bentone 38 particulate clay thickener used in Examples 9, 10 and 11. In each case, the composition of Examples 9, 10 and 11 provided enhanced deposition efficacy as compared to Comparative Examples 1 and 2.

Accordingly, the composition employing the Bentone 27 particulate clay and the bis-vinyl dimethicone/dimethicone copolymer amount of about 0.224 wt % tended to provide the best deposition efficacy for the aerosol antiperspirant composition without providing too high a level, greater than 0.4 wt %, of the bis-vinyl dimethicone/dimethicone copolymer.

What is claimed is:

1. An aerosol antiperspirant composition comprising: at least one active antiperspirant ingredient, a his-vinyl dimethicone/dimethicone copolymer, a silicone solvent, at least one fatty acid ester and at least one propellant.

2. The composition of claim 1 wherein the bis-vinyl dimethicone/dimethicone copolymer is present in an amount of from 0.1 to 0.75 wt % based on the weight of the composition including the at least one propellant.

3. The composition of claim 2 wherein the bis-vinyl dimethicone/dimethicone copolymer is present in an amount of from 0.15 to 0.3 wt % based on the weight of the composition including the at least one propellant.

4. The composition of claim 3 wherein the his-vinyl dimethicone/dimethicone copolymer is present in an amount of from 0.2 to 0.25 wt % based on the weight of the composition including the at least one propellant.

5. The composition of claim 1 wherein the silicone solvent comprises dimethicone.

6. The composition of claim 1 wherein the silicone solvent is present in an amount of from 0.5 to 5 wt % based on the weight of the composition including the at least one propellant.

7. The composition of claim 6 wherein the silicone solvent is present in an amount of from 0.75 to 2 wt % based on the weight of the composition including the at least one propellant.

8. The composition of claim 7 wherein the silicone solvent is present in an amount of from 0.9 to 1.25 wt % based on the weight of the composition including the at least one propellant.

9. The composition of claim 1 wherein the at least one fatty acid ester comprises one or more esters of a C2-C5 alcohol and a C12-C20 fatty acid.

10. The composition of claim 9 wherein the C2-C5 alcohol comprises propyl alcohol.

11. The composition of claim 9 wherein the C12-C20 fatty acid comprises at least one fatty acid selected from myristic acid, palmitic acid and isostearic acid.

12. The composition of claim 9 wherein the at least one fatty acid ester comprises one of more of isopropyl myristate, isopropyl palmitate and isopropyl isostearate.

13. The composition of claim 12 wherein the at least one fatty acid ester comprises a mixture of isopropyl myristate and isopropyl palmitate.

14. The composition of claim 13 wherein the isopropyl myristate and isopropyl palmitate are present in the mixture in a weight ratio of from 0.5:1 to 1:0.5.

15. The composition of claim 14 wherein the isopropyl myristate and isopropyl palmitate are present in the mixture in a weight ratio of about 1:1.

16. The composition of claim 9 wherein the at least one fatty acid ester is present in an amount of from 0.5 to 7.5 wt % based on the weight of the composition including the at least one propellant.

17. The composition of claim 16 wherein the at least one fatty acid ester is present in an amount of from 2 to 5 wt % based on the weight of the composition including the at least one propellant.

18. The composition of claim 17 wherein the at least one fatty acid ester is present in an amount of from 3 to 4.5 wt % based on the weight of the composition including the at least one propellant.

19. The composition of claim 1 further comprising a thickener comprised of an organic derivative of a hectorite clay.

20. The composition of claim 19 wherein the thickener comprises a trialkylaryl ammonium hectorite clay.

21. The composition of claim 19 wherein the thickener comprises quaternium-18 hectorite.

22. The composition of claim 19 wherein the organic derivative of a hectorite day is present in an amount of from 0.2 to 0.4 wt % based on the weight of the composition including the at least one propellant.

23. The composition of claim 22 wherein the organic derivative of a hectorite clay is present in an amount of from 0.25 to 0.35 wt % based on the weight of the composition including the at least one propellant.

24. The composition of claim 1 wherein the at least one active antiperspirant ingredient is selected from aluminium salts, zirconium salts and zinc salts.

25. A method of manufacturing the composition of claim 1, the method including the step of:
 a. providing the bis-vinyl dimethicone/dimethicone copolymer, the silicone solvent, and the at least one fatty add ester as at least one premixed gel; and
 b. mixing the at least one premixed gel with at least the active antiperspirant ingredient.

* * * * *